United States Patent
Agnew

(10) Patent No.: US 9,775,686 B2
(45) Date of Patent: Oct. 3, 2017

(54) DENTAL DAM CLAMP

(71) Applicant: Beverly Agnew, Flagstaff, AZ (US)

(72) Inventor: Beverly Agnew, Flagstaff, AZ (US)

( * ) Notice: Subject to any disclaimer, the term of this patent is extended or adjusted under 35 U.S.C. 154(b) by 0 days.

(21) Appl. No.: 15/362,584

(22) Filed: Nov. 28, 2016

(65) Prior Publication Data

US 2017/0156819 A1    Jun. 8, 2017

Related U.S. Application Data

(60) Provisional application No. 62/263,884, filed on Dec. 7, 2015.

(51) Int. Cl.
*A61C 5/12*    (2006.01)
*A61C 5/82*    (2017.01)

(52) U.S. Cl.
CPC .............. *A61C 5/122* (2013.01); *A61C 5/82* (2017.02); *A61C 2201/00* (2013.01)

(58) Field of Classification Search
CPC ............. A61C 5/80–5/85; A61C 5/122; A61C 2201/00
See application file for complete search history.

(56) References Cited

U.S. PATENT DOCUMENTS

| | | | |
|---|---|---|---|
| 1,166,924 A * | 1/1916 | Newlin | A61C 5/82 433/139 |
| 4,661,063 A | 4/1987 | Levy | |
| 4,773,857 A * | 9/1988 | Herrin | A61C 5/82 433/138 |
| 4,787,849 A * | 11/1988 | Jacoby | A61C 5/82 433/139 |
| 5,503,556 A | 4/1996 | Leonard et al. | |
| 6,206,697 B1 | 3/2001 | Hugo | |
| 7,175,432 B2 | 2/2007 | McDonald | |
| 2005/0147941 A1* | 7/2005 | McDonald | A61C 5/85 433/153 |
| 2008/0064003 A1 | 3/2008 | Clark | |
| 2009/0208901 A1 | 8/2009 | Doenges et al. | |
| 2013/0344455 A1 | 12/2013 | Hull et al. | |
| 2014/0242544 A1 | 8/2014 | Anderson et al. | |

FOREIGN PATENT DOCUMENTS

| | | |
|---|---|---|
| FR | 2820024 A1 | 8/2002 |
| WO | 8304176 | 12/1983 |
| WO | 2014047029 A1 | 3/2014 |

* cited by examiner

*Primary Examiner* — Heidi M Eide
(74) *Attorney, Agent, or Firm* — Booth Udall Fuller, PLC

(57) ABSTRACT

A dental dam clamp and method comprising an aperture frame, a first opposing jaw, and a second opposing jaw is disclosed. The first opposing jaw is coupled to a first opposing end of the aperture frame, and the second opposing jaw coupled to a second opposing end of the aperture frame. The first opposing jaw and the second opposing jaw are biased toward a rest state by the aperture frame. The external surface of the aperture frame comprises at least one notch, and the internal surface of the aperture frame defines a treatment aperture. The aperture frame may be substantially parallel with both the first opposing jaw and the second opposing jaw.

20 Claims, 9 Drawing Sheets

DENTAL DAM CLAMP

RELATED APPLICATIONS

This application claims the benefit of U.S. provisional patent application 62/263,884, filed Dec. 7, 2015 titled "Dental Dam Clamp," the entirety of the disclosure of which is hereby incorporated by this reference.

TECHNICAL FIELD

Aspects of this document relate generally to dental dam clamps.

BACKGROUND

In dentistry, it is often necessary to isolate an area of a patient's mouth, such as around a tooth, or where a tooth should be. Such isolation serves to create a clean, dry area in which a dental procedure may be performed, provides a degree of protection to soft tissue, and protects the patient's airway from debris, components, and dental tools. This isolation can be achieved using the patient's teeth in combination with dental dams, which are well known in the art.

Typically, a dental dam is placed such that the tooth of interest is exposed through a perforation in an elastic sheet called a dam. A dental dam clamp is used to hold the dam in place during the dental treatment. Conventional dental dam clamps, such as those disclosed in U.S. Pat. No. 4,661,063, employ a resilient connector between two jaws that clamp onto the tooth. The resilient connector extends away from the jaws and tooth. Conventional clamps are not effective in some situations, such as when the tooth needing isolation is so broken down to a point where the clamp has nothing to grip.

To isolate a broken down tooth, some conventional clamps can make use of a neighboring tooth, such as the clamp disclosed in U.S. Pat. No. 5,503,566. However, the resilient connector or bias-providing element of such clamps is problematic when used to isolate a posterior edentulous area. In such cases, the resilient connector of the clamp either collides with the back of the mouth or obstructs access to the area, making it difficult or impossible to render the intended dental treatment. Furthermore, the dental treatments commonly rendered to an edentulous area, such as restoration or implant procedures, have a greater need for isolation and protection of the patient's airway due to the debris and components involved.

SUMMARY

According to one aspect, a dental dam clamp includes an aperture frame, a first opposing jaw, and a second opposing jaw. The aperture frame includes an internal surface, an external surface opposite the internal surface, a first opposing end, and a second opposing end. The first opposing jaw is coupled to the first opposing end, and the second opposing jaw is coupled to the second opposing end. The first opposing jaw and the second opposing jaw are both configured to engage a tooth. The first opposing jaw and the second opposing jaw are biased toward a rest state by the aperture frame when in a tension state, the rest state comprising the first opposing jaw separated from the second opposing jaw by a first distance and the tension state comprising the first opposing jaw separated from the second opposing jaw by a separation distance different from the first distance. The external surface of the aperture frame includes at least one notch configured to receive an internal edge of a perforated dental dam. Finally, the internal surface of the aperture frame borders a treatment aperture through which a dental treatment may be rendered.

Particular embodiments may comprise one or more of the following features. The aperture frame may be substantially parallel with both the first opposing jaw and the second opposing jaw. The at least one notch may comprise a recess in the external surface of the aperture frame which may be substantially parallel to the aperture frame. At least one of the at least one notches may extend longitudinally along a majority of the external surface of the aperture frame. Each of the at least one notch may include an upper projection extending away from the aperture frame, a lower projection proximate the upper projection and extending away from the aperture frame, and/or a junction between the upper projection and the lower projection which is proximate the aperture frame and may be configured to receive the internal edge of the perforated dental dam. The external surface may comprise at least a first notch stacked vertically with a second notch. The dental dam clamp may further comprise a forceps socket in each of the first opposing jaw and the second opposing jaw. At least one of the first opposing jaw, the second opposing jaw, and the aperture frame may further comprise a ligature hole extending through the respective at least one of the first opposing jaw, the second opposing jaw, and the aperture frame. At least one of the aperture frame and the position of the at least one notch with respect to the aperture frame may be asymmetrical with respect to a mirror plane extending between the first and second opposing jaws.

According to another aspect, a dental dam clamp includes a first clamp jaw, a second clamp jaw opposing the first clamp jaw and separated from the first clamp jaw by a first distance, and an aperture frame extending between the first clamp jaw and the second clamp jaw. The aperture frame biases the first clamp jaw and the second clamp jaw to a position with a separation distance of the first distance. An external surface of the aperture frame includes at least one notch, and an internal surface of the aperture frame defines a treatment aperture.

Particular embodiments may comprise one or more of the following features. The dental dam clamp may include a forceps socket in each of the first clamp jaw and the second clamp jaw. Furthermore, at least one of the first clamp jaw, the second clamp jaw, and the aperture frame may further include a ligature hole extending through the respective at least one of the first clamp jaw, the second clamp jaw, and the aperture frame. The at least one notch may comprise three notches distributed on the external surface of the aperture frame asymmetrically with respect to the mirror plane between the first and second clamp jaws. Also, the dental dam clamp may be composed of a thermoplastic.

According to yet another aspect of the disclosure, a method for isolating an area inside a treatment aperture using a dental dam clamp comprising a first opposing jaw and a second opposing jaw separated from the first opposing jaw by a first distance, the opposing jaws biased to a position with a separation distance of the first distance by, and coupled to each other through, an aperture frame includes engaging a forceps socket located on each of the first opposing jaw and the second opposing jaw with dental dam clamp forceps. The method also includes spreading apart the first and second opposing jaws by actuating the dental dam clamp forceps, and creating the treatment aperture bordered by an internal surface of the aperture frame and a proximal surface of a tooth adjacent the area by positioning the dental dam clamp such that the first opposing jaw engages with an oral surface of the tooth and the second opposing jaw engages with a vestibular surface of the tooth while the aperture frame is centered above the area. Furthermore, the method includes coupling a perforated dental dam to an external surface of the aperture frame comprising at least one notch by securing an internal edge of a perforation in the perforated dental dam within at least one of the at least one notch. Finally, the method includes stretching the perforated dental dam over the first and second opposing jaws, the perforated dental dam coupling with the dental dam clamp along the external surface of the aperture frame.

Particular embodiments may be modified or adapted such that the area is a posterior edentulous area.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

The invention will hereinafter be described in conjunction with the appended drawings, where like designations denote like elements, and.

DETAILED DESCRIPTION

Figure 1:
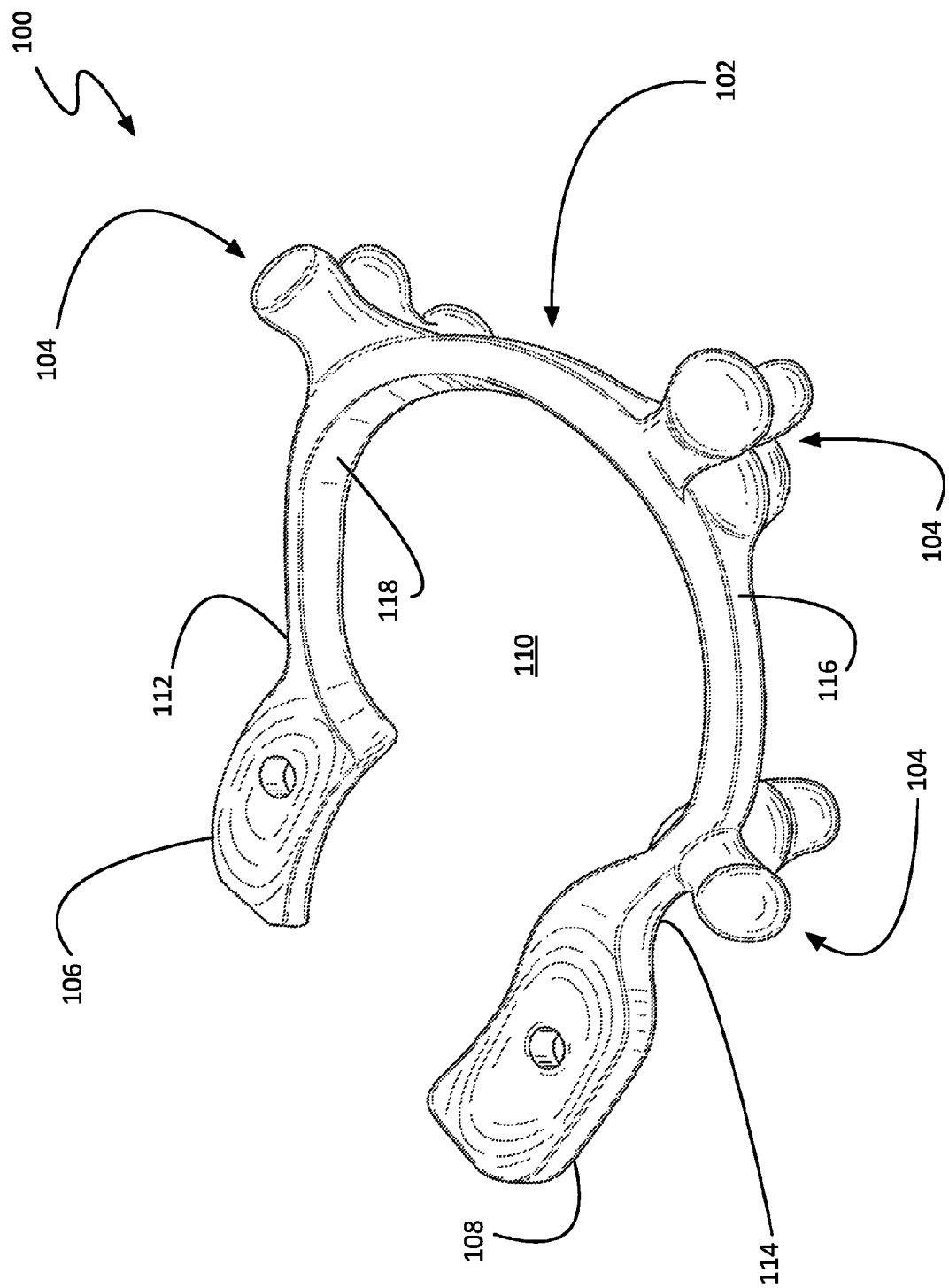
FIG. 1 is a perspective view of a dental dam clamp.

This disclosure, its aspects and implementations, are not limited to the specific dental dam clamps or material types, or other system component examples, or methods disclosed herein. Many additional components, manufacturing and assembly procedures known in the art consistent with dental dam clamp manufacture are contemplated for use with particular implementations from this disclosure. Accordingly, for example, although particular implementations are disclosed, such implementations and implementing components may comprise any components, models, types, materials, versions, quantities, and/or the like as is known in the art for such systems and implementing components, consistent with the intended operation.

The word "exemplary," "example," or various forms thereof are used herein to mean serving as an example, instance, or illustration. Any aspect or design described herein as "exemplary" or as an "example" is not necessarily to be construed as preferred or advantageous over other aspects or designs. Furthermore, examples are provided solely for purposes of clarity and understanding and are not meant to limit or restrict the disclosed subject matter or relevant portions of this disclosure in any manner. It is to be appreciated that a myriad of additional or alternate examples of varying scope could have been presented, but have been omitted for purposes of brevity.

While this disclosure includes a number of embodiments in many different forms, there is shown in the drawings and will herein be described in detail particular embodiments with the understanding that the present disclosure is to be considered as an exemplification of the principles of the disclosed methods and systems, and is not intended to limit the broad aspect of the disclosed concepts to the embodiments illustrated.

FIGS. 1-5 depict different views of non-limiting examples of dental dam clamps. Specifically, these figures depict non-limiting examples of a dental dam clamp 100 comprising an aperture frame 102, a first opposing jaw 106, a second opposing jaw 108, and a treatment aperture 110. The aperture frame 102 comprises at least one notch 104, a first opposing end 112, and a second opposing end 114. As shown, the first opposing jaw 106 (or first clamp jaw) is coupled to the first opposing end 112, and the second opposing jaw 108 (or second clamp jaw) is coupled to the second opposing end 114. The aperture frame 102 couples, and biases, the first opposing jaw 106 and the second opposing jaw 108, as shall be described in greater detail with respect to FIGS. 2A-2B.

As shown, the aperture frame 102 further comprises an external surface 116 and internal surface 118. In the context of the present description and the claims that follow, an external surface refers to a surface of an aperture frame 102 that is, at least in part, in contact with the dental dam being used to isolate an area (e.g. the area 504 of FIGS. 5A-D, etc.) inside a treatment aperture 110. According to various embodiments, the external surface 116 is where the one or more notches 104 of a dental dam clamp 100 are located. In the context of the present description and the claims that follow, an internal surface 118 refers to a surface of an aperture frame 102 that borders a treatment aperture 110.

As shall be discussed in greater detail with respect to FIGS. 5A-5D, a dental dam clamp 100 may be used in conjunction with a perforated dental dam to isolate an area inside a patient's mouth for a dental treatment. Specifically, treatment may be provided through a treatment aperture 110, which is partially bordered by the internal surface 118 of the aperture frame 110, while the rest of the mouth and throat are protected from debris, material, and/or instruments by a dental dam received by one or more notches 104 and coupled to the dental dam clamp 100.

A dental dam clamp 100 comprises at least one notch 104, according to various embodiments. In the context of the present description and the claims that follow, a notch is a portion of a dental dam clamp that can receive an edge of a dental dam (e.g. the internal edge 516 of the perforated dental dam 514 of FIGS. 5C and 5D, etc.). According to various embodiments, a notch 104 may prevent a received edge of a dental dam 514 from shifting with respect to the treatment aperture 110, which may result in an accidental decoupling of the dental dam 514 from the dental dam clamp 100.

Traditionally, dental dams are composed of an elastic material, such as rubber. According to various embodiments, a notch 104 may be shaped such that the contracting force exerted by a stretched dental dam keeps the internal edge 516 of a perforation 518 in the dental dam 514 coupled with the notch 104.

In some embodiments, a notch 104 may extend beyond the external surface 116 of an aperture frame 102. See, for example, the notches 104 shown in FIGS. 1-3. In other embodiments, a notch 104 may be sunken into the external surface 116. See, for example, the notch 104 shown in FIG. 4. A dental dam clamp 100 may comprise a single notch 104, or multiple notches 104. In some embodiments, a dental dam clamp 100 may comprise notches 104 of different designs.

As shown, a dental dam clamp 100 comprises a first opposing jaw 106 and a second opposing jaw 108. According to various embodiments, these jaws are configured to engage, or grip, a tooth such that a dental dam may be secured in place. Specifically, the jaws are configured to engage a tooth (e.g. tooth 500 of FIGS. 5A-5D, etc.)

adjacent to an area meant to be isolated for treatment through the treatment aperture 110 of a dental dam clamp 100. In some embodiments, the jaws may have "wings", under which a dental dam may be tucked to further prevent it from slipping off the dental dam clamp 100. In other embodiments, the jaws may have no wings. Those skilled in the art will recognize that the first opposing jaw 106 and the second opposing jaw 108 shown in FIGS. 1-5 may be replaced with other known dental clamp jaws, which may be of different construction, material, and/or shape.

According to various embodiments, a dental dam clamp 100 may be composed of a variety of materials. Like other dental instruments, the cleanliness of a dental dam clamp 100 is an important consideration. In some embodiments, a dental dam clamp 100 may be composed of materials that can withstand the temperatures associated with common sterilization procedures, such as an autoclave. Examples of materials that can withstand such temperatures include, but are not limited to, stainless steel and high temperature thermoplastics such as polyether ether ketone (PEEK). In other embodiments, a dental dam clamp 100 may be composed of materials that can be sterilized after manufacturing, perhaps using methods unavailable or impractical for a dental practice, and then disposed of after use. Examples of such materials may include, but are not limited to, thermoplastics that may or may not be reinforced with fibers. In some embodiments, a dental dam clamp 100 may be composed of materials that are x-ray transparent, to facilitate dental imaging while the clamp is in use. The jaws of a dental dam clamp 100 may also include materials chosen to better grip the surface of the tooth being engaged, as is known in the art.

Figure 2A:
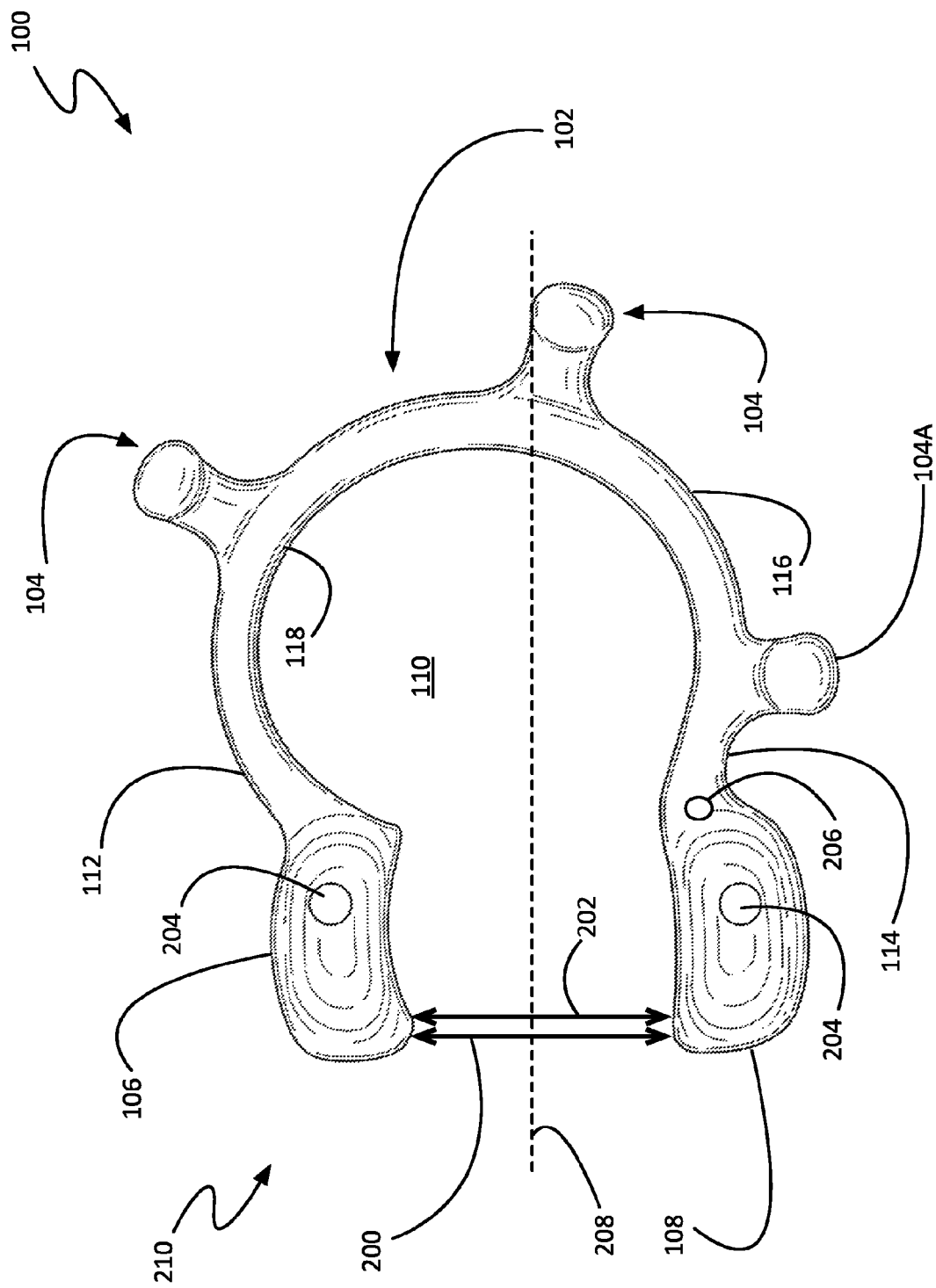
FIG. 2A is a top view of a dental dam clamp in a rest state.
Figure 2B:
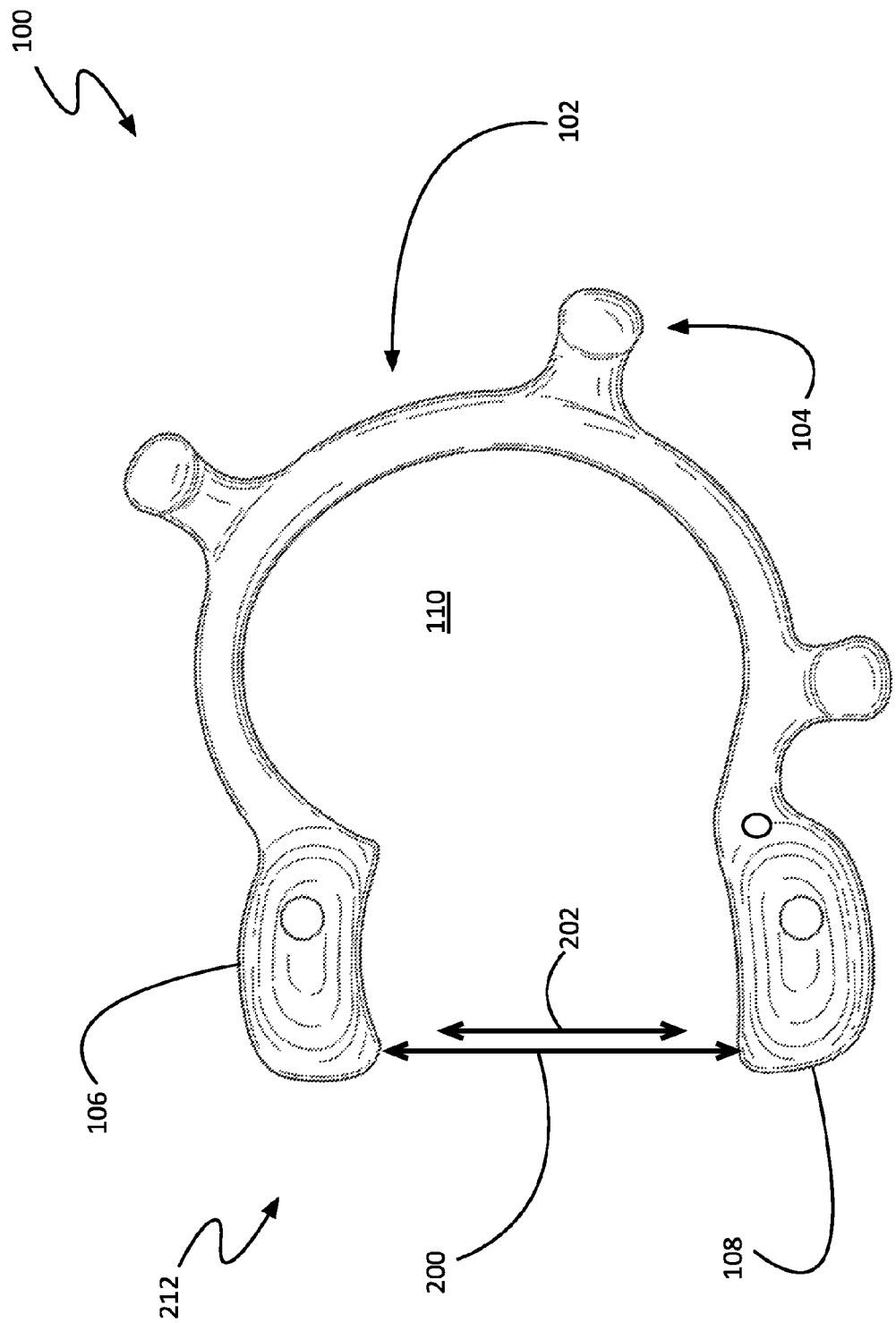
FIG. 2B is a top view of the dental dam clamp of FIG. 2A in a tension state.

FIGS. 2A and 2B illustrate a top view of a non-limiting embodiment of a dental dam clamp 100. FIG. 2A shows a dental dam clamp 100 in a rest state 210. In the context of the present description and the claims that follow, the rest state 210 of a dental dam clamp 100 may be defined as an arrangement of the dental dam clamp 100 such that there are no external forces (e.g. dental clamp forceps, etc.) acting on the jaws to move them apart or together, and no obstructions (e.g. a tooth, etc.) keeping them spread apart. The separation distance 200 between the jaws of a dental dam clamp 100 in a rest state 210 is defined as the first distance 202, as shown in FIG. 2A.

FIG. 2B shows a dental dam clamp 100 in a tension state 212. In the context of the present description and the claims that follow, a tension state 212 of a dental dam clamp 100 may be defined as an arrangement of the dental dam clamp 100 such that the separation distance 200 is not equal to the first distance 202. In other words, a dental dam clamp 100 is in a tension state 212 when it is not in a rest state 210. When in a tension state 212, the aperture frame 102 of the dental dam clamp 100 biases the first opposing jaw 106 and the second opposing jaw 108 toward a separation distance 200 equal to the first distance 202. The aperture frame 102 biases the dental dam clamp 100 towards a rest state 210. This bias allows the jaws to grip a tooth, which may keep the dental dam clamp 100 in place while in use.

As shown in FIGS. 1-5, a dental dam clamp 100 comprises a forceps socket 204 located in each jaw. In the context of the present description and the claims that follow, a forceps socket 204 refers to any structure or aspect of the dental dam clamp 100 that may releasably couple with an end of dental forceps such that the forceps may be used to spread the jaws of the dental clamp apart, putting the clamp in a tension state 212 in preparation for application to a tooth. Those skilled in the art will recognize that the forceps sockets 204 shown in FIGS. 1-5 may be replaced with other known forceps sockets or reception points, which may be of different construction, shape, and/or compatible with different forceps or other dental tools.

The non-limiting example of a dental dam clamp 100 shown in FIGS. 2A and 2B further comprises a ligature hole 206. A ligature hole 206 may be used to secure a ligature to a dental dam clamp 100, as a preventative measure against accidentally losing the clamp down a patient's throat. In some embodiments, a dental dam clamp 100 may have a ligature hole 206 for securing a ligature; in other embodiments, a ligature may be tied around part of the dental dam clamp 100, as is done in traditional dental dam clamps. The use of a ligature hole 206 may be advantageous, though, as it may be less likely to interfere with the seal of the dental dam against the dental dam clamp 100.

According to some embodiments, a dental dam clamp 100 may be symmetrical with respect to a mirror plane 208 running between the first opposing jaw 106 and the second opposing jaw 108, bisecting their separation distance 200, and perpendicular to a plane containing both jaws (hereinafter referred to as mirror plane 208). In other embodiments, a dental dam clamp 100 may be asymmetrical with respect to mirror plane 208. Some embodiments of a dental dam clamp 100 may have an aperture frame 102 that is asymmetrical with respect to mirror plane 208. Other embodiments may comprise one or more notches 104 in locations that are asymmetrical with respect to mirror plane 208. In still other embodiments, both types of asymmetry may be present. See, for example, the non-limiting embodiment shown in FIG. 2A.

As shown in FIG. 2A, the aperture frame 102 may be asymmetrical with respect to the mirror plane 208, according to some embodiments. This may be advantageous, as the asymmetry may allow the dental dam clamp 100 to follow the curvature of a patient's teeth, such that the treatment aperture 110 may be centered over an area such as the posterior edentulous area 506 shown in FIGS. 5B-D while the jaws are gripping an adjacent tooth 500. Furthermore, an asymmetric arrangement of notches 104, such as that shown in FIG. 2A, may also be advantageous. The lowest notch shown in FIG. 2A, labeled notch 104A, is located on the vestibular side of the external surface 116 of the dental dam clamp 100. Movement of a patient's lip or cheek may dislodge a dental dam; having notch 104A on the vestibular side of the clamp 100 may serve to better prevent a dental dam from becoming dislodged during treatment. The oral side of the clamp may not have such a need, or may have that need but in a different location, such as at or near the point where the aperture frame 102 extends the furthest into the oral cavity.

A dental dam clamp 100 may be adapted for the isolation of a variety of areas in a patient's mouth. Teeth vary in size and relative location to each other, and a dental dam clamp 100 may be adapted in consideration of these variations. Parameters which may be adjusted to optimize a dental dam clamp 100 for a particular location in a mouth include, but are not limited to, the first distance 202, the shape and/or symmetry of the aperture frame 102, the number, size, and/or type of notches 104, the size of the treatment aperture 110, and the strength of the elasticity of the aperture frame 102 which affects the tooth-gripping strength of the first and second opposing jaws. The treatment aperture 110 of a dental dam clamp 100 may vary in size such that sufficient room is available for a dental treatment to be performed without interfering with other objects (e.g. teeth, tongue, etc.) in the mouth. In some embodiments, the treatment aperture 110 may be roughly circular, and may have a largest diameter between ½" and 1". In another embodiment, the treatment aperture 110 may be roughly ¾" in diameter. In still other embodiments, the treatment aperture 110 may have other sizes and/or shapes advantageous to particular dental treatments or particular locations within a mouth.

Figure 3:
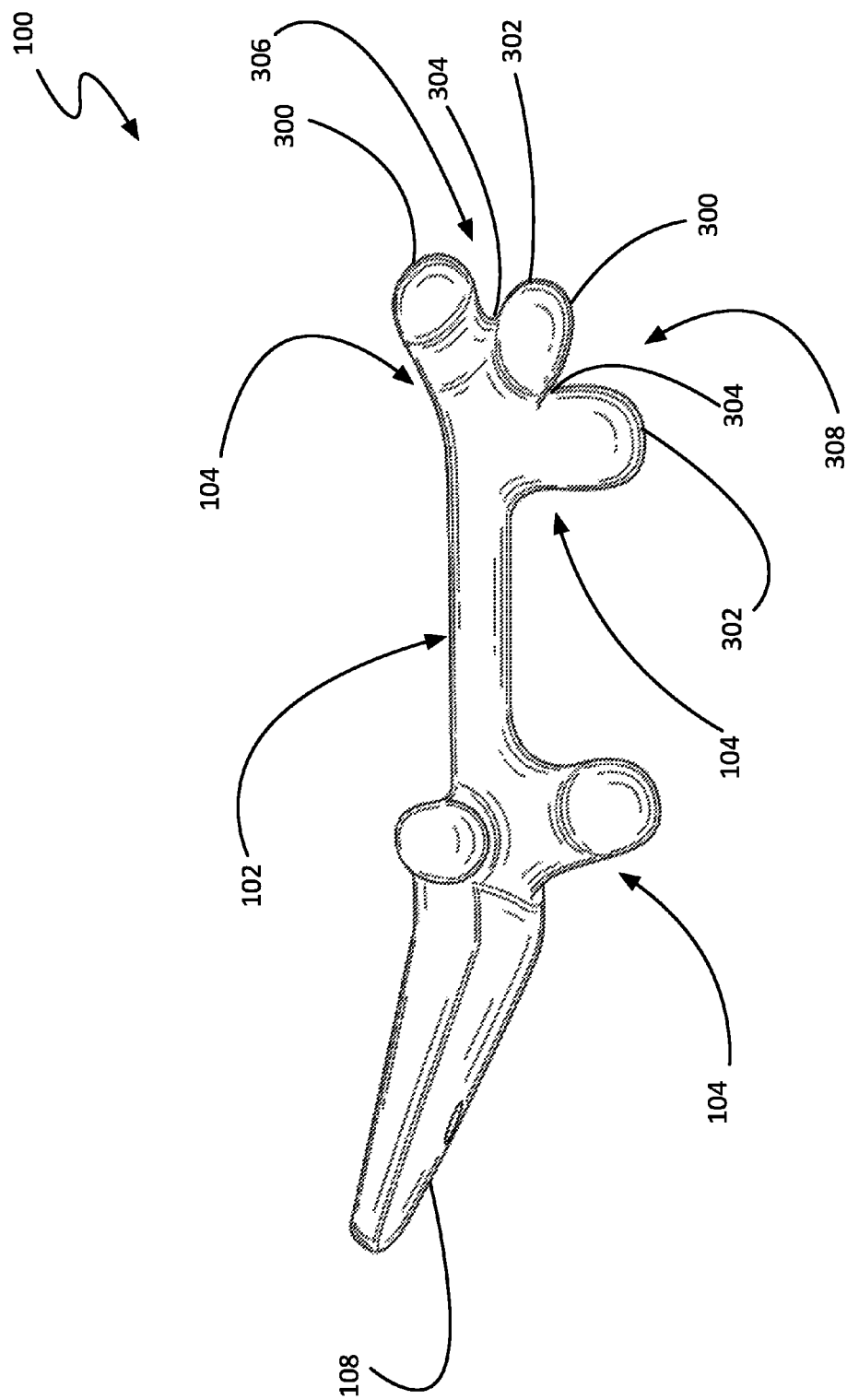
FIG. 3 is a side view of a dental dam clamp.

FIG. 3 illustrates a side view of a non-limiting embodiment of a dental dam clamp 100. As shown, a notch 104 may comprise an upper projection 300, a lower projection 302, and a junction 304 between the upper projection 300 and the lower projection 302, according to various embodiments. The junction 304 of a notch 104 is configured to receive an edge (e.g. internal edge 516 of FIGS. 5C-D, etc.) of a dental dam. Once the junction 304 of a notch 104 has received an edge of a dental dam, the upper projection 300 and the lower projection 302 will prevent the dental dam from sliding up and over, or down and under, the dental dam clamp 100.

In some embodiments, two or more notches 104 may be stacked vertically, allowing a user a choice of depth for the dental dam. For example, the dental dam clamp 100 of FIG. 3 demonstrates a first notch 306 stacked vertically with a second notch 308. In various embodiments, a lower projection 302 of one notch (e.g. the first notch 306, etc.) may also serve as an upper projection 300 of another notch (e.g. the second notch 308).

The type of notch 104 demonstrated in the non-limiting embodiment of a dental dam clamp 100 shown in FIG. 3 may be advantageous in certain circumstances. The upper projection 300 may facilitate the application of a perforated dental dam by providing a "hook" to catch the internal edge of a perforation in the dental dam. Some dental professionals prefer to apply a dental dam clamp before affixing a dental dam; the upper projection 300 of a notch 104 like those shown in FIG. 3 may provide an easy first point of attachment. The use of a dental dam clamp 100 will be discussed in greater detail with respect to FIGS. 5A through 5D.

In traditional dental dam clamps, the tension-providing element is often perpendicular, or near perpendicular, to the tooth-gripping element. As shown in FIG. 3, the aperture frame 102 of a dental dam clamp 100 may be substantially parallel with both the first opposing jaw 106 and the second opposing jaw 108, according to various embodiments. In the context of the present description and the claims that follow, "substantially parallel" means within 30° of each other.

Figure 4:
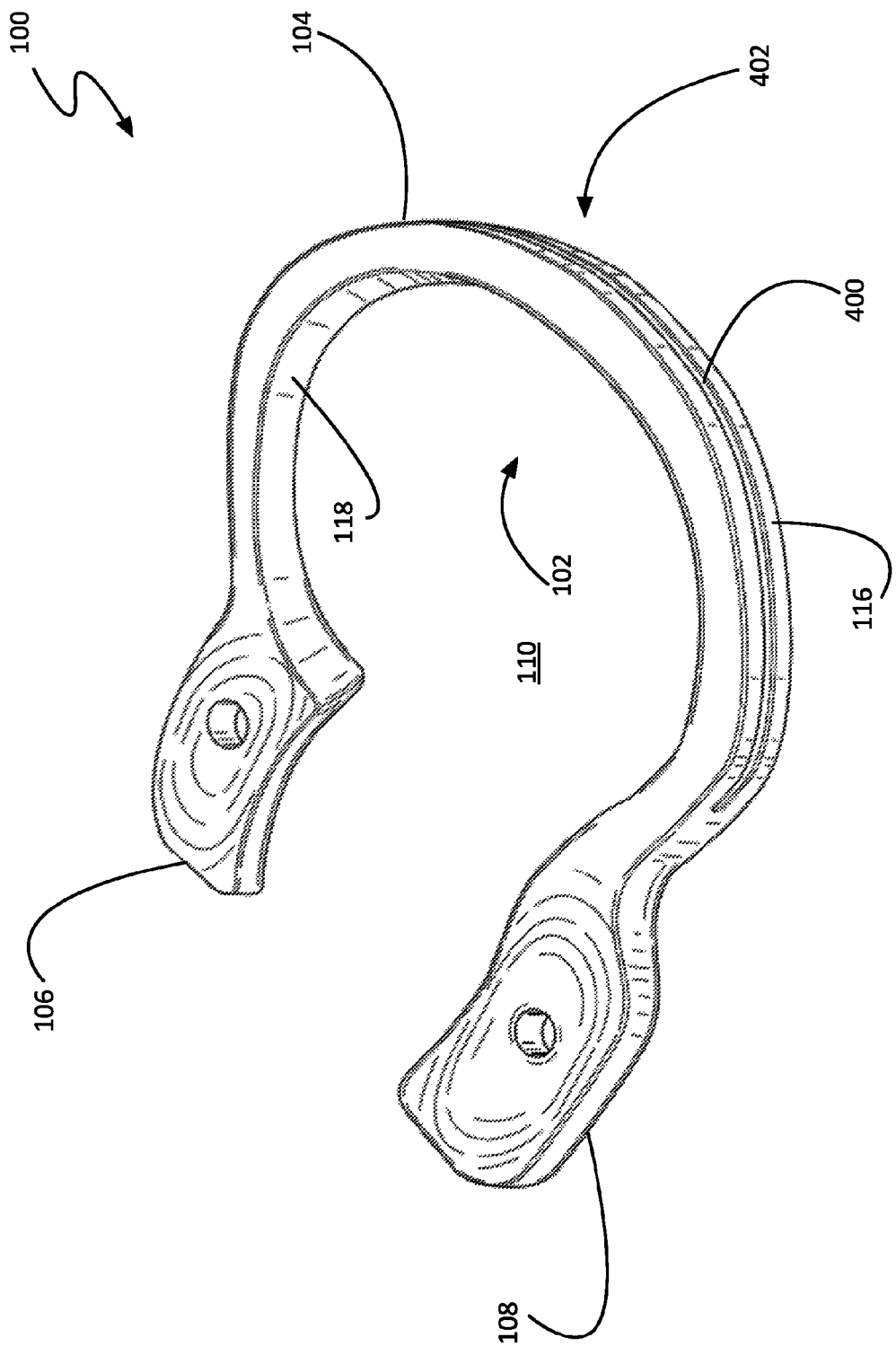
FIG. 4 is a perspective view of a dental dam clamp.

The notches 104 having an upper projection 300 and a lower projection 302 shown in FIG. 3 are a non-limiting example of a notch 104 of a dental dam clamp 100, according to some embodiments. In other embodiments, a notch 104 like the one shown in FIG. 4 may be employed. FIG. 4 illustrates a perspective view of a non-limiting embodiment of a dental dam clamp 100. As shown, a notch 104 may comprise a recess 400 in an external surface 116 of a dental dam clamp 100. The recess 400 of a notch 104 is configured to receive an edge (e.g. internal edge 516 of FIGS. 5C-D, etc.) of a dental dam.

According to various embodiments, a notch 104 may extend along a portion of the external surface 116 of an aperture frame 102. For example, as shown in FIG. 4, a notch 104 may extend longitudinally along a majority 402 of the external surface 116. In the context of the present description and the claims that follow, to extend longitudinally along an external surface 116 of an aperture frame 102 means to extend along a path which resides in a plane that is substantially parallel to the plane of the aperture frame 102. Furthermore, in the context of the present description and the claims that follow, to be substantially parallel means to have a relative angle between 0° and 30°. In other embodiments, a notch 104 may extend along a majority 402 of an external surface 116, but may do is in a manner which is not "longitudinally" (e.g. does not extend along a path which resides in a plane, etc.).

In some embodiments, a notch 104 having a recess 400 may be substantially parallel to the aperture frame 102 in which it resides. See, for example, the non-limiting embodiment shown in FIG. 4. In other embodiments, a recess 400 may be angled with respect to the aperture frame 102. This may be done to better line up with the lowest portion of the first and second opposing jaws (106 and 108, respectively). Lining up the endpoints of a recess 400 with the lowest parts of the jaws may reduce any upward or downward strain on an internal edge of a perforated dental dam as it transitions from the recess 400 to tuck under the lowest part of the jaws.

The type of notch 104 demonstrated in the non-limiting embodiment of a dental dam clamp 100 shown in FIG. 4 may be advantageous in certain circumstances. Using a notch 104 comprising a recess 400 may result in a dental dam clamp 100 with a smaller profile than clamps employing notches that project above the aperture frame, such as the non-limiting example shown in FIG. 3. A low profile clamp may be desirable for patients where space is limited, such as children. Furthermore, having a single notch 104 that extends longitudinally along a majority of an external surface 116 of an aperture frame 102 may provide a better seal than clamps 100 having multiple notches 104 which secure a dental dam at discrete points. However, the price of a better seal may be the ease with which a dental dam may be applied to projecting notches.

In some embodiments of a dental dam clamp 100, more that one type of notch 104 may be employed. For example, in one embodiment, the "recessed notch" of FIG. 4 may be used in conjunction with notch 104A of FIG. 2A; the protruding notch may be placed on the vestibular side of the clamp to provide additional protection against contact with a patient's cheek. In other embodiments, other types of notches may be employed. For example, in one embodiment, a notch 104 having both a recess as well as angled protrusions may run longitudinally along a majority of the external surface 116 of an aperture frame 102.

FIGS. 5A through 5D illustrate a non-limiting example of a dental dam clamp 100 being used with a perforated dental dam 514 to isolate an area 504 in preparation for a dental treatment. FIGS. 5A-5D show a clamp 100 being used to isolate a posterior edentulous area 506, an application for which the dental dam clamp 100 is well suited. Isolating a posterior edentulous area for treatment is problematic using traditional clamps, particularly due to the tension-providing member, hereinafter referred to as the spring. A clamp would be attached to a tooth adjacent to the edentulous area, as there may not be enough tooth in the edentulous area to support a clamp, and may interfere with treatment. If a traditional clamp is attached so the spring is on the anterior side of the area, the spring will block access to the area, inhibiting treatment. Furthermore, the traditional clamp may not fit in the mouth if the spring is on the posterior side of the area, where it may collide with the patient's mouth and/or other teeth, in addition to being difficult to apply. By using the aperture frame 102 as both a tension-providing member as well as the boundary of a treatment aperture 110, these problems may be avoided by using a dental dam clamp 100 such as the non-limiting examples shown in FIGS. 1-5.

While the dental dam clamp 100 is well suited for use with a posterior edentulous area, it should be clear to those skilled in the art that the dental dam clamp 100 may be employed to isolate other areas of a patient's mouth, and may be used in conjunction with a variety of dental treatments, not limited to work performed on edentulous zones. For example, a dental dam clamp 100 may be useful for dental implant work, particularly implant placement and restoration. Traditional clamps rely on interfacing with the boney contours of a tooth for grip; an implant lacks these boney contours. However, a dental dam clamp 100 may be attached to the boney contours of an adjacent tooth and isolate the area around the implant for treatment.

FIGS. 5A through 5D show a non-limiting example of steps to using a dental dam clamp 100 to isolate an area 504 for dental treatment, according to various embodiments. These figures show the application of the clamp 100 to a tooth 500, and then the application of a dental dam 514. It should be noted that it is also common among dental professionals to stretch a perforated dental dam 514 around a dental clamp, such as dental dam clamp 100, before applying the clamp to a patient's tooth. It should be clear to those skilled in the art that the dental dam clamps 100 disclosed herein may be used in either sequence.

Furthermore, it is common for a dental dam 514 to also be attached to a frame, to keep the dental dam material spread taut over the patient's mouth and throat. Such a frame has been omitted from both figures and discussion, for simplicity. It will be readily apparent that use of such a frame may be incorporated into the methods described. The methods and dental dam clamps described herein may also be used with any elastic dental dam known in the art.

Figure 5A:
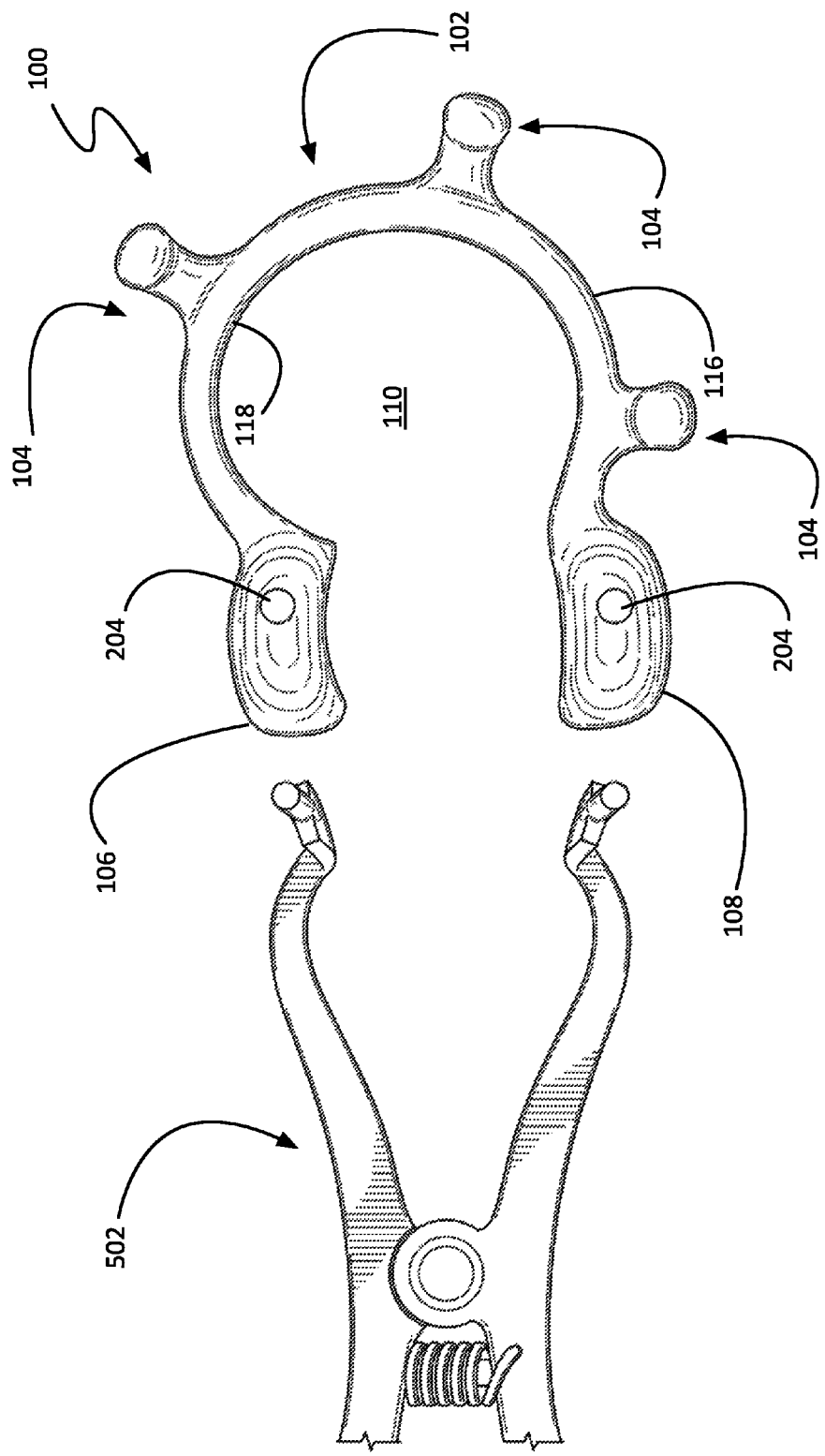
FIGS. 5A-D are top views of a dental dam clamp being used to isolate a posterior edentulous area.

As shown in FIG. 5A, dental dam clamp forceps 502 are used to engage forceps sockets 204 located on the first opposing jaw 106 and the second opposing jaw 108 of a dental dam clamp 100. As previously discussed, the forceps sockets 204 and/or the dental dam clamp forceps 502 may be replaced with any socket/forceps combination known in the art. The dental dam clamp 100 is taken from a rest state 210 to a tension state 212 by spreading the jaws apart by actuating the dental dam clamp forceps 502, such that the separation distance 200 between the jaws is large enough to receive a tooth.

Figure 5B:
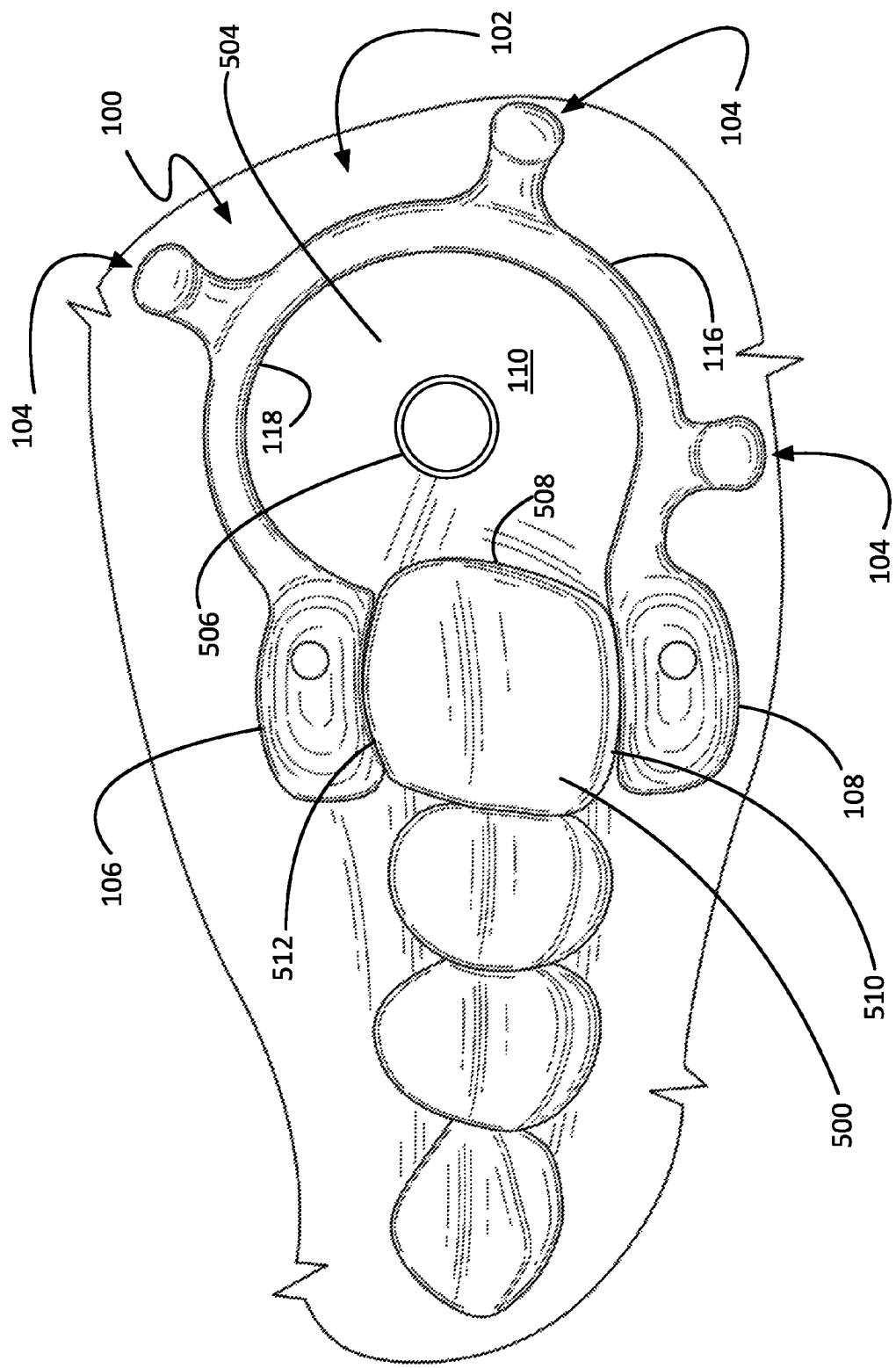

As shown in FIG. 5B, the dental dam clamp 100 is positioned such that the aperture frame 102 is positioned above the area 504 to be isolated, in this case a posterior edentulous area 506. Specifically, the clamp 100 is positioned such that the aperture frame 102 is centered above the area 504, framing it. The forceps 502 are released and removed, such that the first opposing jaw 106 engages with an oral surface 512 of a tooth 500 adjacent to the area 504, and the second opposing jaw 108 engages with a vestibular surface 510 of the tooth 500. As shown, engaging the tooth 500 with the clamp jaws forms a treatment aperture 110 bordered by an internal surface 118 of the aperture frame 102 and a proximal surface 508 of the tooth 500. It is through this treatment aperture 110 that the area 504 may be accessed for treatment.

Figure 5C:
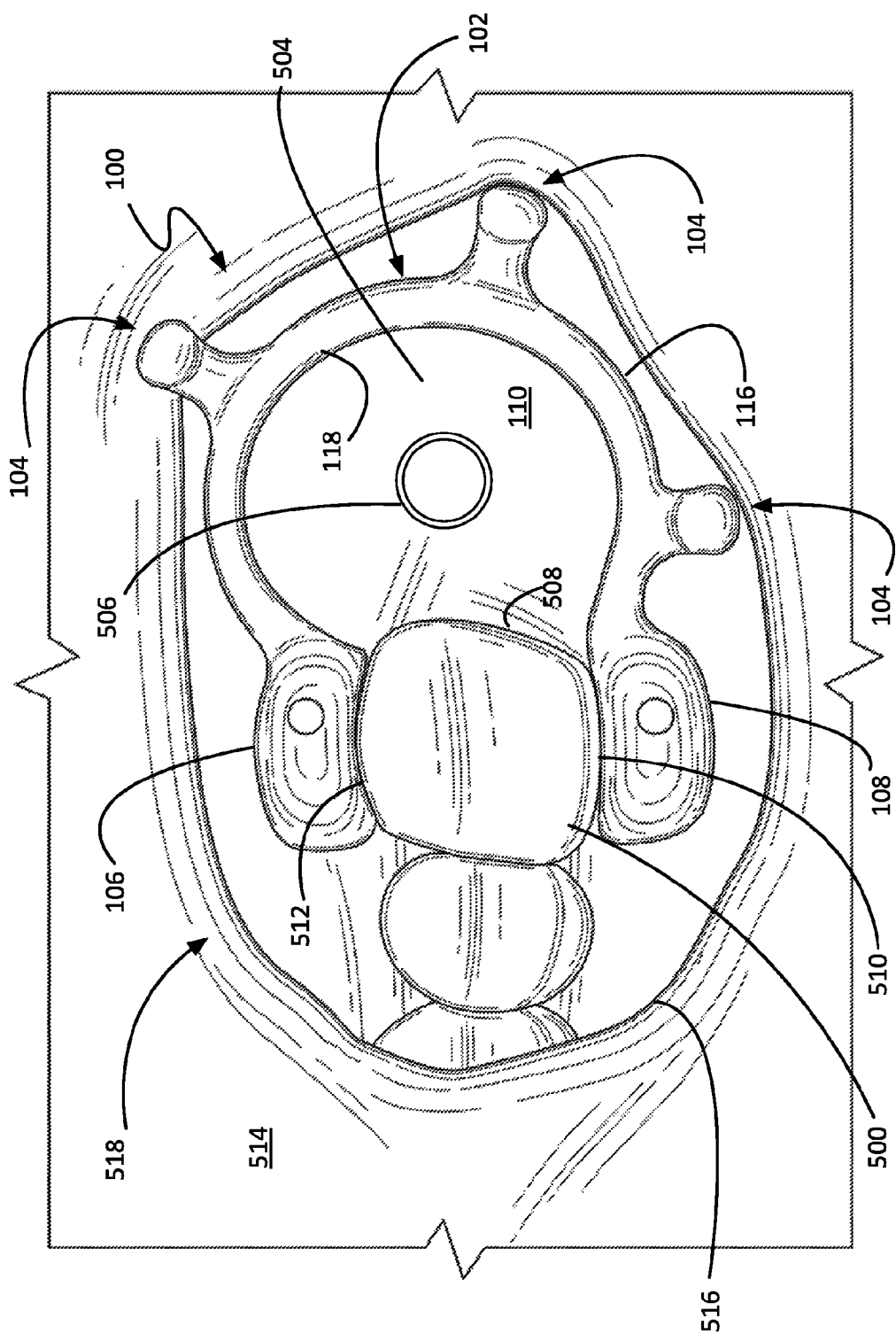
Figure 5D:
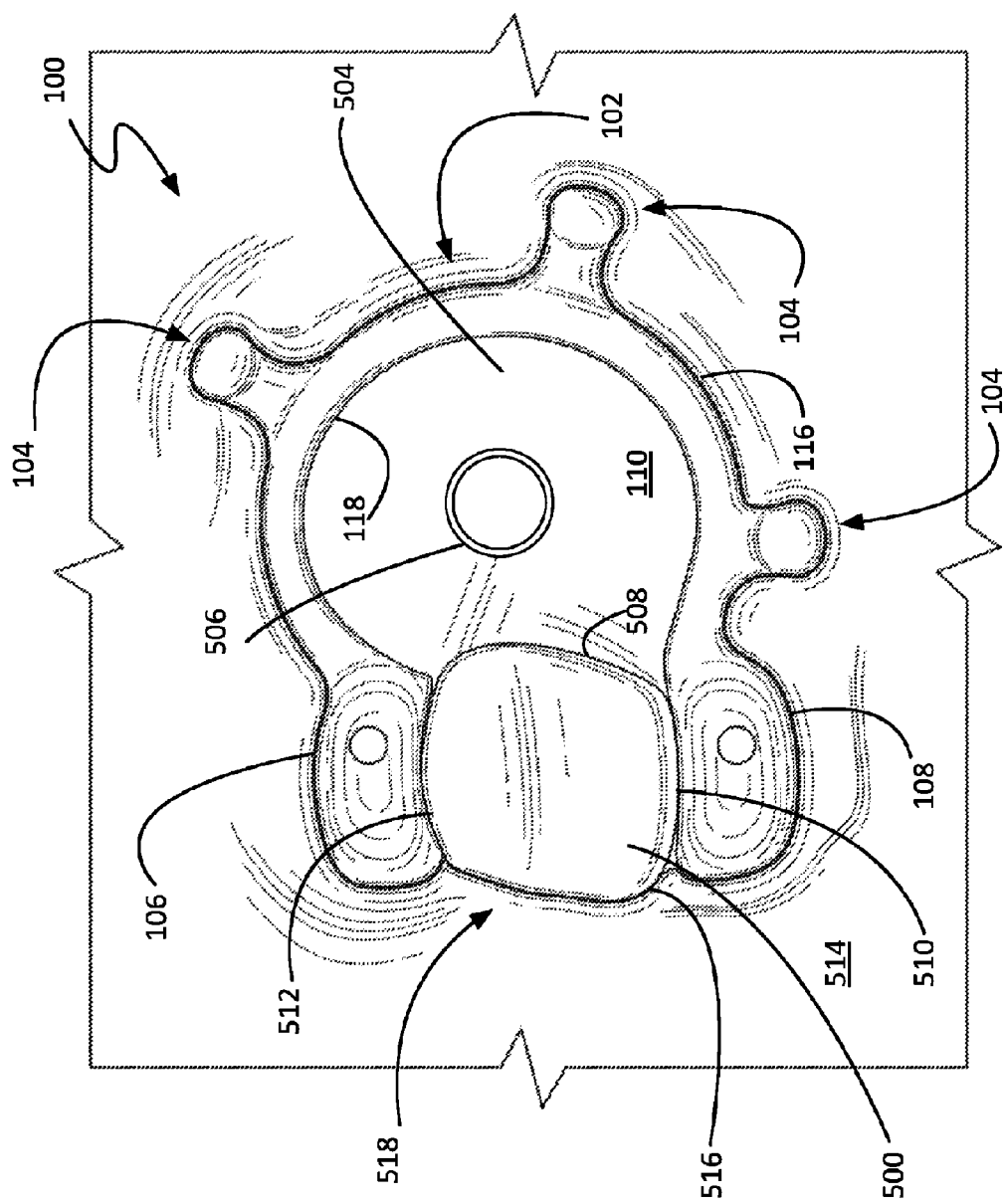

As shown in FIGS. 5C and 5D, a perforated dental dam 514 is coupled to an external surface 116 of the aperture frame 102 by securing an internal edge 516 of a perforation 518 in the dental dam 514 within at least one notch 104 and then stretched over the first and second opposing jaws. The dental dam 514 contracts, forming a seal around the tooth 500 and the dental dam clamp 100, isolating the treatment aperture 110 so treatment may be administered to the area 504.

Where the above examples, embodiments and implementations reference examples, it should be understood by those of ordinary skill in the art that other dental dam clamps and examples could be intermixed or substituted with those provided. In places where the description above refers to particular embodiments of dental dam clamps and application methods, it should be readily apparent that a number of modifications may be made without departing from the spirit thereof and that these embodiments and implementations may be applied to other dental clamps as well. Accordingly, the disclosed subject matter is intended to embrace all such alterations, modifications and variations that fall within the spirit and scope of the disclosure and the knowledge of one of ordinary skill in the art.

What is claimed is:

1. A dental dam clamp, comprising:
    an aperture frame, the aperture frame comprising an internal surface, an external surface opposite the internal surface, a first opposing end, and a second opposing end;
    a first opposing jaw coupled to the first opposing end and comprising a concave internal surface; and
    a second opposing jaw coupled to the second opposing end and comprising a concave internal surface;
    wherein the first opposing jaw and the second opposing jaw are both configured to engage opposing sides of a tooth;
    wherein the first opposing jaw and the second opposing jaw comprise a rest state wherein the first opposing jaw is separated from the second opposing jaw by a first distance, and a tension state wherein the first opposing jaw is separated from the second opposing jaw by a separation distance greater than the first distance;
    wherein the aperture frame is substantially parallel with both the first opposing jaw and the second opposing jaw;
    wherein the external surface of the aperture frame comprises at least one notch configured to receive an internal edge of a perforated dental dam; and
    wherein the internal surface of the aperture frame borders a treatment aperture through which a dental treatment may be rendered.

2. The dental dam clamp of claim 1 wherein the at least one notch comprises a recess in the external surface of the aperture frame which is substantially parallel to the aperture frame.

3. The dental dam clamp of claim 1, wherein at least one of the at least one notch extends longitudinally along a majority of the external surface of the aperture frame.

4. The dental dam clamp of claim 1:
    wherein the at least one notch comprises:
        an upper projection extending away from the aperture frame;
        a lower projection proximate the upper projection and extending away from the aperture frame; and
        a junction between the upper projection and the lower projection which is proximate the aperture frame and configured to receive the internal edge of the perforated dental dam.

5. The dental dam clamp of claim 1, wherein the at least one notch comprises a first notch and a second notch and the external surface comprises the first notch stacked vertically with the second notch.

6. The dental dam clamp of claim 1, further comprising a forceps socket in each of the first opposing jaw and the second opposing jaw.

7. The dental dam clamp of claim 6, wherein at least one of the first opposing jaw, the second opposing jaw, and the aperture frame further comprise a ligature hole extending through the respective at least one of the first opposing jaw, the second opposing jaw, and the aperture frame.

8. The dental dam clamp of claim 1, wherein at least one of the aperture frame and the position of the at least one notch with respect to the aperture frame is asymmetrical with respect to a mirror plane extending between the first and second opposing jaws.

9. The dental dam clamp of claim 1, wherein the treatment aperture includes a dimension larger than the separation distance.

10. A dental dam clamp, comprising:
a first clamp jaw and a second clamp jaw opposing the first clamp jaw and separated from the first clamp jaw by a first distance, wherein the first clamp jaw and the second clamp jaw each comprise a concave internal surface; and
an aperture frame extending between the first clamp jaw and the second clamp jaw, the aperture frame biasing the first clamp jaw and the second clamp jaw to a position with a separation distance of the first distance, wherein an external surface of the aperture frame comprises at least one notch, wherein the aperture frame is substantially parallel with the first clamp jaw and the second clamp jaw, and wherein an internal surface of the aperture frame defines a treatment aperture.

11. The dental dam clamp of claim 10 wherein the at least one notch comprises a recess in the external surface of the aperture frame which is substantially parallel to the aperture frame.

12. The dental dam clamp of claim 10, wherein at least one of the at least one notch extends longitudinally along a majority of the external surface of the aperture frame.

13. The dental dam clamp of claim 10:
wherein the at least one notch comprises:
an upper projection extending away from the aperture frame;
a lower projection proximate the upper projection and extending away from the aperture frame; and
a junction between the upper projection and the lower projection which is proximate the aperture frame and configured to receive the internal edge of the perforated dental dam.

14. The dental dam clamp of claim 13, wherein the treatment aperture includes a dimension larger than the first distance.

15. The dental dam clamp of claim 10, further comprising:
a forceps socket in each of the first clamp jaw and the second clamp jaw;
wherein at least one of the first clamp jaw, the second clamp jaw, and the aperture frame further comprise a ligature hole extending through the respective at least one of the first clamp jaw, the second clamp jaw, and the aperture frame.

16. The dental dam clamp of claim 10, wherein at least one of the aperture frame and the position of the at least one notch with respect to the aperture frame is asymmetrical with respect to a mirror plane extending between the first and second clamp jaws.

17. The dental dam clamp of claim 16, wherein the at least one notch comprises three notches distributed on the external surface of the aperture frame asymmetrically with respect to the mirror plane between the first and second clamp jaws.

18. The dental dam clamp of claim 10, wherein the dental dam clamp is composed of a thermoplastic.

19. A method for isolating an area inside a treatment aperture using a dental dam clamp comprising a first opposing jaw and a second opposing jaw separated from the first opposing jaw by a first distance, the opposing jaws biased to a position with a separation distance of the first distance by, and coupled to each other through, an aperture frame, the method comprising:
engaging a forceps socket located on each of the first opposing jaw and the second opposing jaw with dental dam clamp forceps;
spreading apart the first and second opposing jaws by actuating the dental dam clamp forceps;
creating the treatment aperture larger than a tooth adjacent the area and bordered by an internal surface of the aperture frame and a proximal surface of the tooth adjacent the area by positioning the dental dam clamp with the aperture frame substantially parallel with both the first opposing jaw and the second opposing jaw such that the first opposing jaw engages with an oral surface of the tooth and the second opposing jaw engages with a vestibular surface of the tooth while the aperture frame is centered above the area;
coupling a perforated dental dam to an external surface of the aperture frame comprising at least one notch by securing an internal edge of a perforation in the perforated dental dam within at least one of the at least one notch; and
stretching the perforated dental dam over the first and second opposing jaws, the perforated dental dam coupling with the dental dam clamp along the external surface of the aperture frame.

20. The method of claim 19, wherein the area is a posterior edentulous area.

* * * * *